United States Patent [19]
Rosenthal et al.

[11] Patent Number: 6,093,393
[45] Date of Patent: Jul. 25, 2000

[54] METHODS FOR PREPARING AND USING CLONOGENIC FIBROBLASTS AND TRANSFECTED CLONOGENIC FIBROBLASTS

[76] Inventors: Felicia Rosenthal, Schillerstrasse 32, 79102 Freiburg; Albrecht Lindemann, Bürgleweg 18d, 79294 Sölden; Thomas Boehm, Utzengasse 10, 79279 Vörstetten; Roland Mertelsmann, Sonnhalde 72, 79104 Freiburg; Hendrik Veelken, Schlippehof 8, 79110 Freiburg; Peter Kulmburg, Gauberhof 5, 79110 Freiburg, all of Germany

[21] Appl. No.: 08/700,506

[22] PCT Filed: Feb. 23, 1995

[86] PCT No.: PCT/EP95/00660

§ 371 Date: Aug. 22, 1996

§ 102(e) Date: Aug. 22, 1996

[87] PCT Pub. No.: WO95/23216

PCT Pub. Date: Aug. 31, 1995

[30] Foreign Application Priority Data

Feb. 24, 1994 [DE] Germany ............... 44 06 073

[51] Int. Cl.[7] ............... A61K 35/12; C12N 15/63; C12N 15/85; C12N 5/02
[52] U.S. Cl. ............... 424/93.21; 435/347; 435/455; 435/458; 435/461; 424/93.2
[58] Field of Search ............... 514/44; 424/93.21, 424/93.2; 435/320.1, 172.3, 325, 375, 347, 455, 458, 461; 935/52

[56] References Cited

U.S. PATENT DOCUMENTS 4,423,145 12/1983 Stampfer et al. ............... 435/32
4,804,627 2/1989 Hammerling et al. ............... 435/240.21

FOREIGN PATENT DOCUMENTS 9307906 4/1993 WIPO.

OTHER PUBLICATIONS

Crystal, R.G. et al, (1995), Science 270: 404–410.
Panis et al. (1992) C.R. Acad. Sci. Paris 315: 541–544.
Fireshney, R.I. (1988) 'A Manual of Basic Technique' 2nd Edition, Alan R. Liss, Inc. New York pp. 107–126.
Fereshney, R.I. (1988) 'A Manual of Basic Technique' 2nd Edition, Alan R. Liss, Inc. New York pp. 107–126.
Tani et al (1989) Blood 74: 1274–1280.
Marshall E (1995) Science 269: 1050–1055.
Miller et al (1995) Faseb J. 9: 190–199.

*Primary Examiner*—Scott D. Priebe

[57] ABSTRACT

The invention relates to a process for preparing clonogenic fibroblasts, with tissue being removed from the donor and the individual cells being isolated from the tissue, the resulting cell suspension being strained, the cells which are contained in the cell suspension being washed and the cells being converted into a tissue culture, with the exception of the isolation of individual cells by mechanical comminution, followed by an enzymic treatment with collagenase alone, and with at least one gene being inserted into the fibroblasts by means of the transfection, which gene encodes a biologically active protein, preferably a therapeutically active protein, for example a growth factor, a hormone, an enzyme, a coagulation factor or a coagulation inhibitor.

23 Claims, 14 Drawing Sheets

|  | Monocytes ||| Granulocytes ||| Lymphocytes |||
|---|---|---|---|---|---|---|---|---|---|
|  | Cyclo | GM-CSF | CMS5/GM-CSF | Cyclo | GM-CSF | CMS5/GM-CSF | Cyclo | GM-CSF | CMS5/GM-CSF |
| d0 | 100 | 100 | 100 | 3000 | 2500 | 1400 | 6800 | 7300 | 8500 |
| d5 | 0 | 0 | 0 | 0 | 0 | 10 | 1000 | 1000 | 990 |
| d7 | 75 | 630 | 495 | 725 | 2070 | 1340 | 1700 | 1800 | 2070 |

FIG. 8

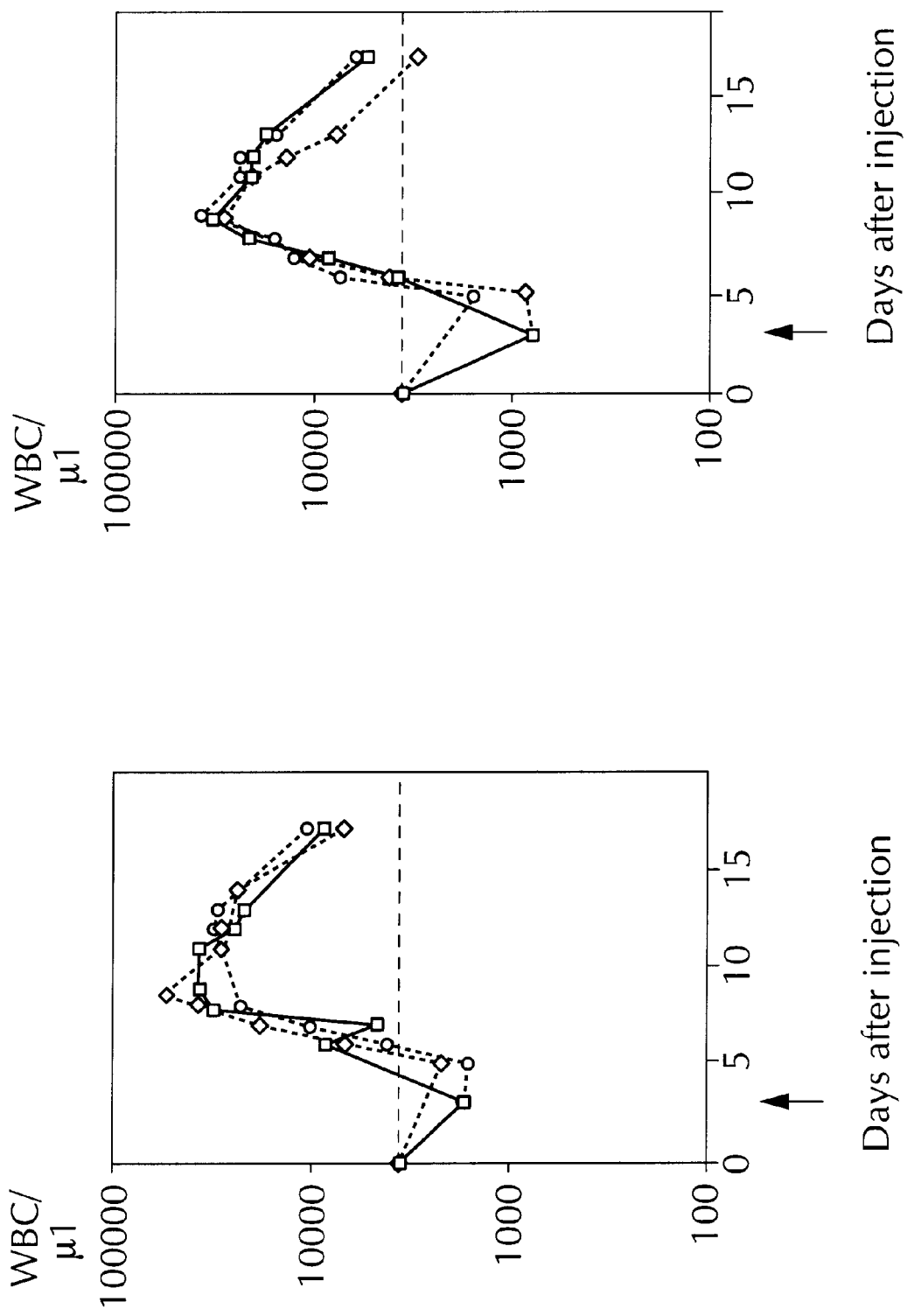

METHODS FOR PREPARING AND USING CLONOGENIC FIBROBLASTS AND TRANSFECTED CLONOGENIC FIBROBLASTS

The present invention relates to a process for preparing clonogenic fibroblasts, to processes for genetically transfecting fibroblasts and to genetically transfected fibroblasts which are thus obtained.

In the therapy of a wide variety of diseases, it is desirable to supply particular biologically active molecules, which can also be produced by the human body, to the body in an increased, medicinally active dose. However, the medicinal supply of biologically active molecules which have been prepared outside the body also has the disadvantage that such active compounds have to be administered parenterally frequently and often even several times daily, with a single, subcutaneous administration often not being sufficient and intravenous doses which are administered several times daily being required instead.

SU 13 17 021 A1 relates to diploid stem cells from human skin and to embryonic muscle cells which have been isolated for the purpose of cultivating viruses.

SU 15 18 370 A1 relates to embryonic stem cell cultures of human skin and muscles for the purpose of producing diagnostic preparations.

Chapter 9 of the handbook written by R. Jan Freshney, "Culture of Animal Cells", 2nd Edition, Alan R. Liss Inc., New York, 1988, describes the isolation of tissue and primary (cell) cultures. On the following pages, a process for preparing human fibroblasts is described in which the tissue has been removed from the skin of donors within the context of a biopsy, whereupon the individual cells are isolated from the tissue, the cells which are present in the cell suspension are washed and the cells are converted into a tissue culture. However, this process comprises, exclusively within the context of isolating cells, a mechanical isolation of cells followed by an enzymic treatment with collagenase.

An object of the present invention is to provide a process by which cells of this nature are made available which have been altered in such a way that they are able to produce biologically active molecules.

The present invention discloses a process for preparing human clonogenic fibroblasts and also a process for genetically transfecting fibroblasts.

BRIEF DESCRIPTION OF THE FIGURES

FIG. 8 depicts production of GM-CSF from irradiated populations on days 0, 5, and 7. The table gives the absolute value of the leucocyte subpopulations on treatment days 0, 5, and 7. Cyclo=cyclophosphamide, d0+d2 (i.p., 150 mg/kg). GM-CSF=cyclophosphamide, d0+d2 (i.p., 150 mg/kg)+rmGM-CSF, d3–d10 (s.c., 100 ηg, 2×daily). CMS5/GM-CSF=cyclophosphamide, d0+d2 (i.p., 150 mg/kg)+N2/CMV-GM-CSF/CMS5, d3 (s.c., $10^7$ cells).

FIGS. 10C and 10D depict the leucocyte counts following inoculations of tumor cells and gancyclovir.

FIGS. 11 A, B, C, and D depict the leukocyte numbers following chemotherapy and cytokine therapy in the presence or absence of transfected fibroblasts. FIG. 11C, Cyclophosphamide+G-CSF/BALB 3T3. FIG. 11D, Cyclophosphamide+irradiated G-CSF/BALB 3T3.

Figure 1:
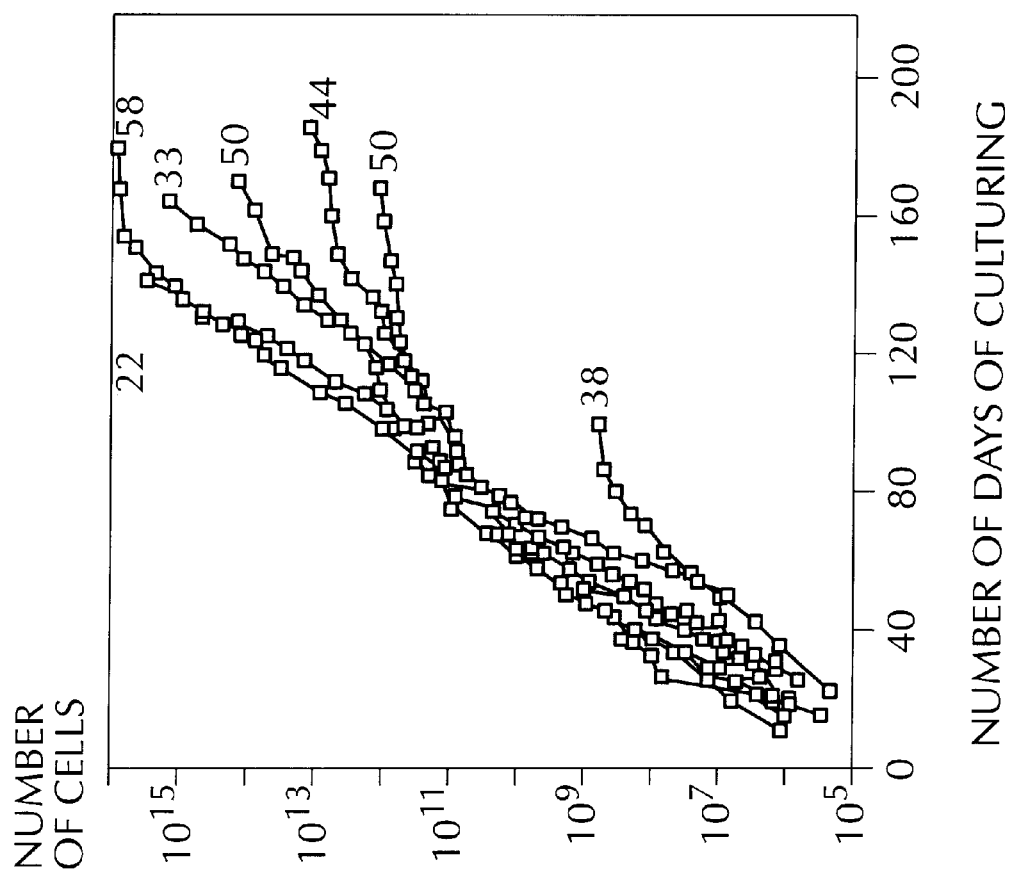
FIG. 1 depicts the mean doubling time of cell cultures prepared from various donors. The numbers behind the curves indicate the age of the respective donors.

In the novel processes, tissue samples are first removed from the serosa and, in a preferred form, from the skin of the donor, with these samples having a size of from 0.5 to about 2 cm². Tissue samples of this nature can be removed using known, routine surgical biopsy methods.

The samples which are obtained within the context of the biopsy are then chopped with a scalpel or a comparable instrument into pieces of less than 2 mm in diameter. These pieces can then be laid out on cell culture plates with the epidermal layer upwards. In a preferred manner, Dulbecco's modified Eagle's medium (DMEM) containing 10% fetal calf serum and the customary additives can be used as the culture medium.

Within the context of the present invention, it has emerged that it is more advantageous if the tissue samples are first of all only chopped down to a size of about 0.5 cm² and these pieces are then incubated in culture medium (DMEM), with the medium containing enzymes which promote isolation of the individual cells. Within the scope of the present invention, collagenase, dispase (a neutral protease) or hyaluronidase are preferably employed as enzymes of this nature which promote isolation of the individual cells, with it being possible to use the enzymes either individually or in different combinations.

The cells which have been liberated as a result of the enzymic treatment are then washed with a phosphate-buffered solution of sodium chloride and sown in cell culture bottles at a density of about 2×10⁻⁴/cm².

The fibroblast cultures are customarily provided with fresh growth medium twice a week. When the cultures have reached confluence, the cells can be harvested by treating them with trypsin/EDTA. A new growth cycle begins after the cells have been washed, counted and sown once again at a density of $1 \times 10^4$ cells/cm².

It has emerged that, within the context of the present invention, it is advisable to add so-called feeder cells (about $5 \times 10^5$ cells) to about $10^2$ clonogenic fibroblast cells in dishes having a diameter of 10 cm whereby the efficiency of plating can be improved to up to 9–24%. The feeder cells are irradiated with an intensity of about 50 Gy or 100 Gy. In a preferred manner, human embryonic Ws-1 fibroblasts, which can be obtained from the American Type Culture Collection, or else mouse NIH3T3 fibroblasts, are used for this purpose.

In a particularly effective process for preparing human clonogenic fibroblasts, the tissue samples which are obtained by biopsy are first of all chopped into pieces which are not more than 0.5 cm² in size. These tissue pieces are then digested, at 4° C. for 16 hours, with the enzyme dispase at a concentration of 2.5 units/ml. After the epidermis has been removed, the skin cells are chopped into pieces which are only a few millimeters in size. The material which has thus been obtained is subjected to further digestion, at 37° C. for 3 hours in a shaking water bath, with a mixture of collagenase (200units/ml) and hyaluronidase (300units/ml). Finally, the cells are strained through a sieve having a mesh size of 70 μm, washed and transferred to the cell culture.

It was established that it was possible to obtain about $10^{11}$ cells, after an average time of 89 days (±8 days), from donors who were younger than 60 years old.

FIG. 1 shows that the mean doubling time is about 4.3 (±0.6) days. Further growth was markedly slower in some cases and in quite a number of cases a plateau was reached which allowed no further increase in the cell count. However, in a quite a number of cultures, it was possible to reach a cell count of more than $10^{15}$ cells without any flattening of the curve being observed. It was found that the cultures originating from older donors have slower growth rates and stagnate sooner.

Figures 2A, 2B, 2C:
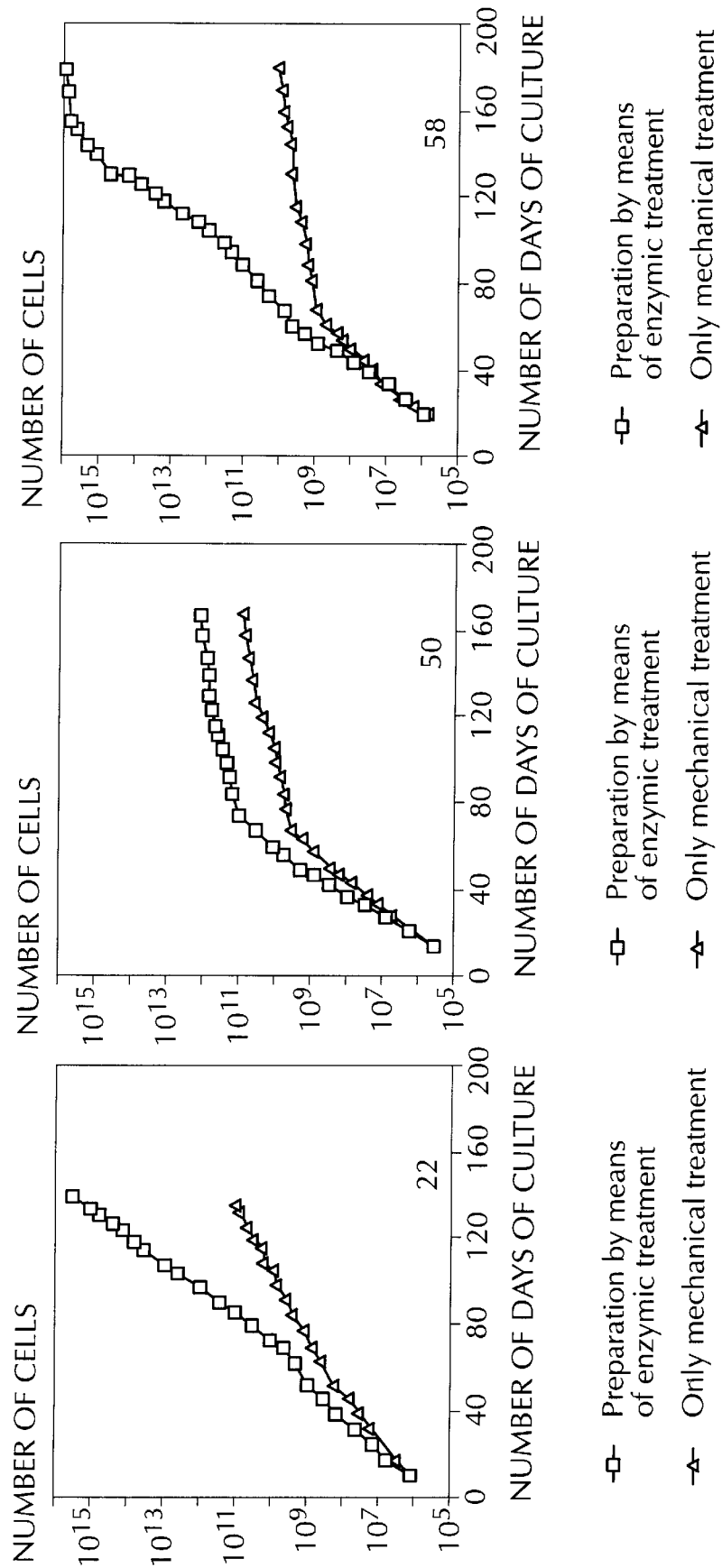
FIGS. 2A–2F depict a comparison of proliferation of fibroblasts as a function of the manner in which the cells were prepared. The numbers in the lower light hand corners indicate the age of the donor.
Figures 2D, 2E, 2F:
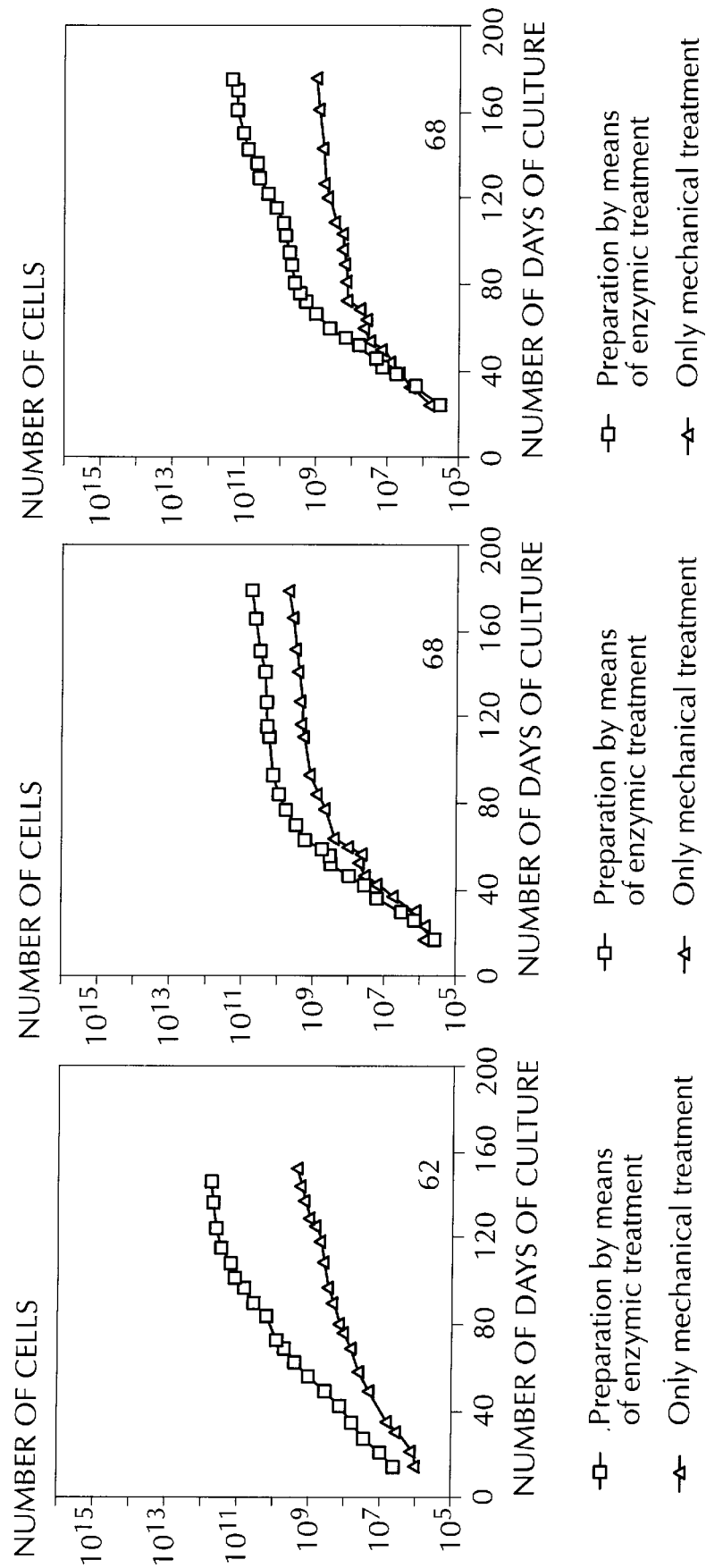

FIG. 2 shows a comparison of fibroblasts as a function of the manner in which the cells were prepared. The enzymically prepared fibroblasts clearly exhibited a greater ability to proliferate than did those which were only obtained from skin biopsies by mechanical preparation. The cell cultures originating from different donors always exhibited superior multiplication behavior when the cells were prepared following an enzymic treatment as compared with those cells which only grew out of the biopsy samples.

Figures 3A, 3B:
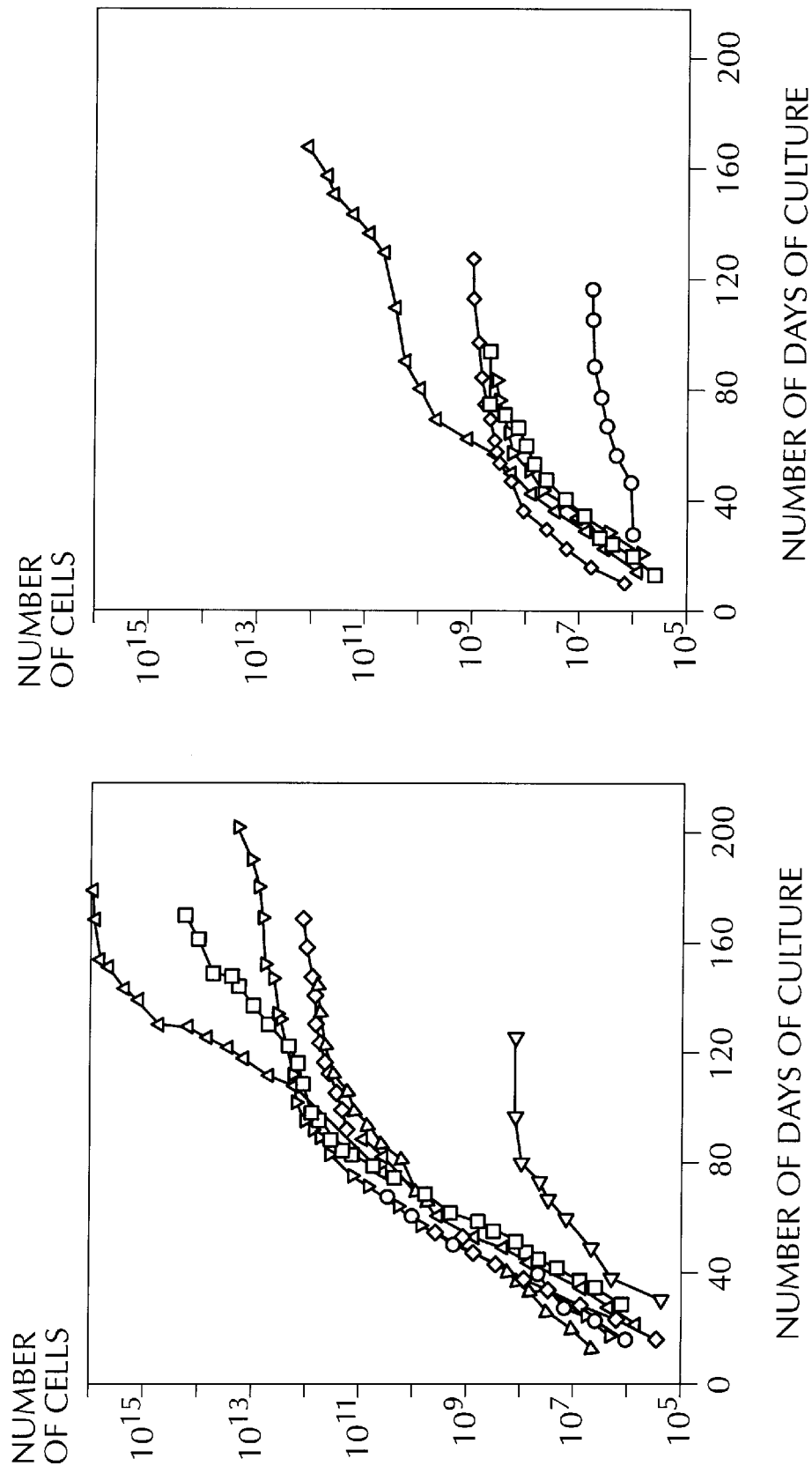
FIGS. 3A (skin) and 3B (serosa) depict the proliferation of autologous fibroblasts from peritoneal cells.

FIG. 3 shows that it was also possible to obtain autologous fibroblasts effectively from peritoneal cells using the enzymic preparation method. While serosa and skin cultures initially grew at equal rates, the diploid fibroblasts from serosa reached the plateau sooner than did skin cultures of the same age.

Figure 4B:
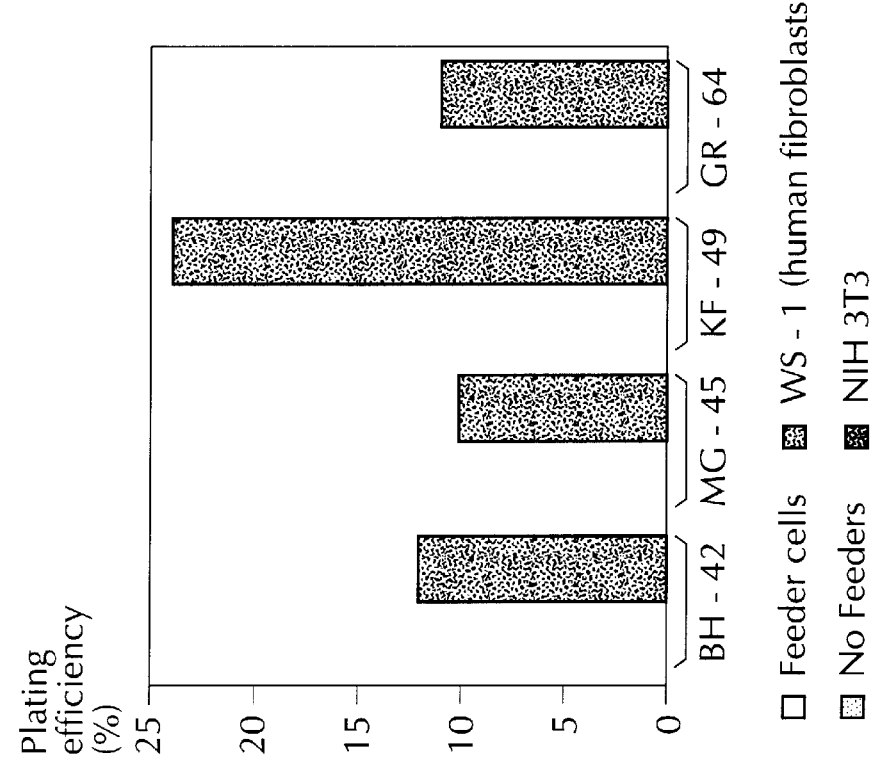
FIGS. 4A and 4B depict the growth of diploid fibroblasts in the presence and absence of feeder cells.
Figure 4A:
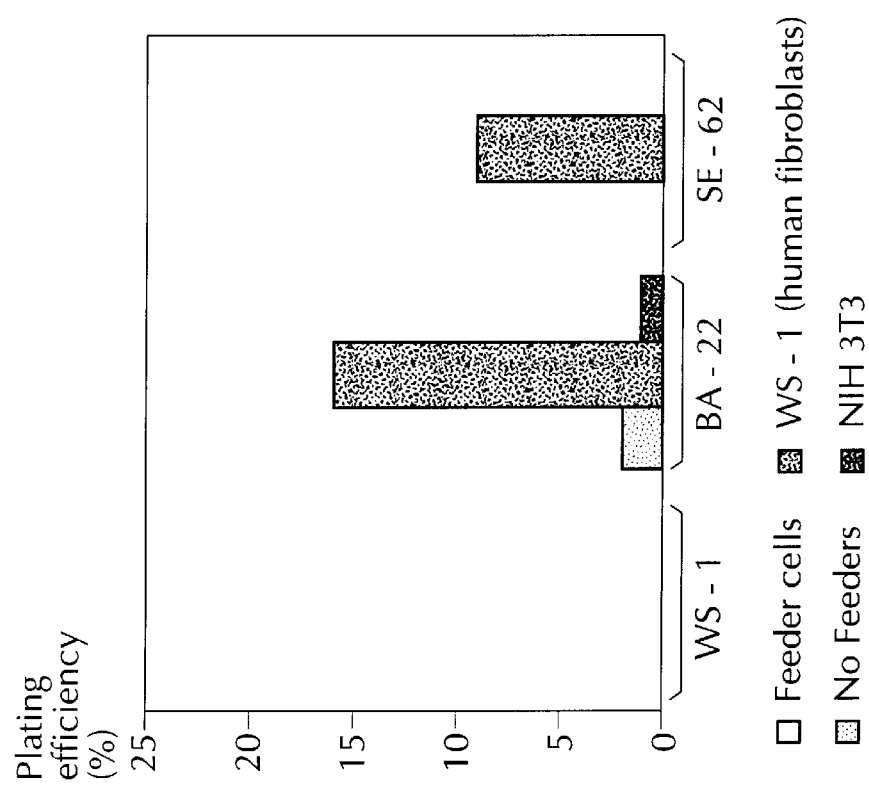

The plating efficiency of the diploid fibroblasts is of great importance with regard to permanently transfected clones. FIG. 4 shows that diploid fibroblasts only grew poorly in the absence of feeder cells. The plating efficiency was increased to from 9 to 24% by adding irradiated human WS-1 fibroblasts. The supernatants from non-irradiated cells were harvested after 3 and 8 days, as were those from cells which were irradiated with 20 Gy and 100 Gy. From 1.2 ng to 20.5 ng of interleukin-6 were found per 24 hours and $10^6$ cells in the supernatants of non-irradiated diploid fibroblasts. The irradiation did not cause any significant change in interleukin-6 secretion. By contrast, non-irradiated diploid fibroblasts produced negligible quantities of GM-CSF (granucyte macrophage colony stimulating factor) or TNFα (tumor necrosis factor), whereas up to 90 pg of GM-CSF and 50 pg of TNFα were measured per 24 hours and $10^6$ cells in the supernatants after irradiation. The induction of these cytokines by irradiation was strongly dependent on the particular individual cultures.

The diploid fibroblasts which can be prepared by the novel process may, for example, be readily obtained from cancer patients. These clonogenic fibroblasts serve as a suitable starting material for the gene transfection. Transfected fibroblasts of this nature may then be supplied once again to the donors as autologous cells.

The fibroblasts which can be obtained by the process which has been described in detail above may be genetically manipulated by means of transfection. During the gene transfection, one or more genes encoding a gene product which is therapeutically valuable are inserted into the clonogenic fibroblasts. Gene products of this nature are growth factors, in particular hematopoietic growth factors, and also hormones, for example insulin, or coagulation factors, for example factor VIII, coagulation inhibitors, enzymes, for example lysosomal enzymes, or adenosine deaminase.

In a particularly preferred embodiment of the present invention, hematopoietic growth factors such as G-CSF or erythropoietin are inserted into the fibroblasts by means of the transfection.

Suitable vectors are required for the transfection. In a preferred embodiment of the present invention, a retroviral vector is used. In addition to the requisite essential genes from the retroviral system, this vector can also contain a so-called suicide gene such as the thymidine kinase gene originating from herpes simplex virus. This enables cells to be selectively destroyed in the presence of gancyclovir. In addition, the vectors can contain inducible promoters which make it possible to regulate gene expression.

A vector which may preferably be used is the retroviral vector N2, which is derived from the genome of the Moloney murine leukemia virus (MLV) and contains, as a selective marker, a bacterial gene for resistance to neomycin. The origin of the fragments and the restriction enzymes which were used to obtain DNA fragments encoding human interleukin-2, mouse interferon-y and herpes simplex virus thymidine kinase promoter and other genes, have already been described [Gansbacher et al., J. Exp. Med., 172 (1990) pp. 1217–1224; Gansbacher et al., Cancer Res., 50 (1990) pp. 7820–7825 and Gansbacher et al., Blood, 80 (1992) pp. 2817–28251].

An additional vector which may preferably be employed in the present process was described in Science, Vol. 256, April 1992, p. 445. This is the outer envelope of an adenovirus in which the adenoviral genes have either been deleted or inactivated in some other way. An antibody possessing a lysine tail is bonded to the viral envelope with the lysine tail bonding to the transfecting DNA. In this vector system, the DNA is not packed within the viral envelope but attached externally to the viral envelope. This vector enables relatively large DNA fragments to be transfected.

The human clonogenic fibroblasts which are obtained in accordance with the novel process may be transfected using the above-described methods. Since only clonogenic fibroblasts are suitable as target cells for stable gene transfection, the fibroblasts which have been obtained in this way are very suitable for expressing foreign genes.

For example, fibroblasts which have been transfected with cytokine genes can be employed as so-called bystander cells in the context of vaccinations against tumors or else for the prophylaxis of infections. Fibroblasts which are transfected with other genes can be reintroduced into the donor and used for supplying the organism over a long period with those molecules which are lacking in the relevant disease. In this context, the molecule can, for example, be blood coagulation factor VIII, protein S or protein C, or else insulin, erythropoietin or other hematopoietic growth factors. It is also possible to provide enzymes such as glucocerebrosidase or adenosine deaminase.

The novel fibroblasts may be used either in an autologous system or else in an allologous system, provided this is possible from the immunological point of view.

According to a preferred embodiment, the genetically transfected fibroblasts are obtained by means of a physical method of gene transfer. Typical examples of such physical methods of gene transfer are electroporation, microinjection, particle bombardment and anionic or cationic lipofection.

An electroporation is, for example, carried out as follows: A quantity of $4 \times 10^6$ cells is washed twice with a phosphate-buffered solution of sodium chloride, [lacuna] in 0.5 ml of an electroporation buffer (20 mmol of HEPES, 137 mmol of sodium chloride, 5 mmol of potassium chloride, 0.7 mmol of $Na_2HPO_4$, 6 mmol of sucrose and 1 mg/ml bovine serum albumin, pH 7.0; (Goldstein et al., Nucleic Acids Research, Vol. 17 (1989), pages 3959 to 3971)) and incubated on ice for 10 minutes, in a 0.4 cm electroporation cuvette from Bio-Rad, Munich, Germany, together with 20 µg of a DNA. The cells are then electroporated with a capacity of 960 µF in an electroporation device which is charged with 250 V. After a second incubation on ice for 10 minutes, the cells are introduced into a 50 ml cell culture vessel containing a normal nutrient solution.

A typical cationic lipofection proceeds, for example, as followsg On the day before the transfection, the cells are applied, at a density of $10^5$ per well, to a 35 mm Petri dish, for example from Falcon. In order to obtain the transfection complexes, 2 µg of the DNA, are added, together with different proportions of lipofection agents (DOSPA/DOPE 3:1), which can be obtained from Gibco in Germany, to 200 µl of DMEM and the whole is incubated at room temperature for 30 minutes. The cells are thereupon washed twice with DMEM and the transfection complexes are added to the cells after having been diluted with DMEM to 1 ml. After an hour, 1 ml of a customary culture medium is added and the medium is changed completely 24 hours later.

The genetically transfected fibroblasts which are obtained in accordance with the invention may be employed as medicaments, in particular for in-vivo treatment. In this context, the genetically transfected fibroblasts can be used, for example, to mobilize hematopoietic stem cells, insofar as a growth factor gene is present.

The present invention furthermore relates to a support which is made out of a biocompatible material which can preferably be used in endoprostheses and which contains the above-described genetically transfected fibroblasts. In this context, the genetically transfected fibroblasts are first cocultured in vitro with the biocompatible material and the material which has been overgrown in this way is then implanted. According to a preferred embodiment of the present invention, the endoprosthesis is a vessel prosthesis which is made out of a biocompatible, preferably human-compatible, synthetic material, for example fluoropolymers or a polyester, and the genetically transfected fibroblasts are implanted in vivo using this prosthesis. Alternatively, the endoprosthesis in the form of a vessel prosthesis can consist of a biocompatible, preferably human-compatible material which is derived from natural sources, for example a collagen fleece or a material obtained from bovine pericardium, with the genetically transfected fibroblasts being implanted in vivo using this prosthesis.

In a preferred embodiment of the present invention, the fibroblasts which are obtained in accordance with the novel process are cocultured with collagen-coated polyvinylpyrrolidone matrices and applied intraperitoneally (i.p.) or subcutaneously (s.c.) in this form as an organoid. It is known that such objects are neovascularized in vivo. The quantity of the gene product which is required in vivo is regulated through the quantity of cells transfected and, where appropriate, also by means of the inducible promoter. Instead of the polyvinylpyrrolidone matrices, other suitable support substances such as fluoropolymer fibers, in particular polytetrafluoroethylene fibers, may also be used, which substances are then overlaid with a suitable coating agent such as collagen. These fibers can then be embedded in an extracellular gel matrix and applied intraperitoneally, for example, by means of a minor surgical operation.

EXAMPLE 1 a) Biopsies

Using routine surgical operations, samples of skin and serosa of about 0.5–2 $cm^2$ in size were obtained from 50 donors who were suffering from cancer. The biopsy samples were stored in Dulbecco's modified Eagle's medium (DMEM) and subjected to further processing on the day they were removed.

b) Mechanical treatment

The biopsy samples were cut with a scalpel into pieces of less than 2 mm in diameter. These pieces were then plated out on cell culture plates with the epidermis upwards. DMEM (Gibco BRL) which contained a high content of glucose and 10% fetal calf serum (Boehringer Mannheim), and which was enriched with L-glutamine and sodium pyruvate, was used as the growth medium.

c) Enzymic treatment

After the biopsy samples had been cut into pieces of less than about 0.5 $cm^2$, these samples were incubated with DMEM medium which contained collagenase (Biochrom, Berlin), dispase (Boehringer Mannheim) or hyaluronidase (Sigma, Deisenhofen) either individually or in different combinations. Cells which were released into the suspension by this treatment were washed with a phosphate-buffered solution of sodium chloride and plated out in cell culture bottles at a density of $2 \times 10^4/cm^2$.

d) Long-term culture

The fibroblast cultures were raised at 37° C. in a moist atmosphere containing 5% $CO_2$, with fresh growth medium being added twice a week. As soon as the cultures reached confluence, the cells were harvested by treating them with trypsin/EDTA, then washed, counted and sown again at a density of $1 \times 10^4$ cells/$cm^2$. The cell counts were extrapolated at each passage starting from the number of cells and the dilution factor.

e) Plating efficiency 100 cells were plated out in 10 cm diameter culture plates. On the following day, $5 \times 10^5$ human embryonic WS-1 fibroblasts or NIH3T3 mouse fibroblasts were added to each culture plate. The two cell lines, both of which are obtainable from the ATCC, Rockville, MD, were used as so-called feeder cells after having been irradiated with 100 Gy. After 4 weeks of culture, the colonies were stained with 2% methylene blue in 50% ethanol and counted, with the medium being changed every 2 weeks during the culture period.

f) Determination of the cytokines

The supernatants from subconfluent cultures were harvested 24 hours after completely changing the nutrient medium. The cells were counted and the cytokine concentrations in the supernatants were determined using commercially available ELISA tests.

EXAMPLE 2

The experimental conditions given in Example 1 were employed using different enzymes (Example 1c) in order to ascertain efficacy for setting up long-term cultures of diploid fibroblasts. The best results were obtained when the biopsy samples, which had been chopped into small pieces, were first digested with dispase at a concentration of about 2.5 U/ml at 4° C. for 16 hours. After this treatment, the epidermis was easily removed from the cell fragments. The skin cells were then further chopped into pieces of a few mm. This cell material was subjected to a second enzymic treatment, at 37° C. for 3 hours in a shaking water bath, using a mixture of collagenase (200 U/ml) and hyaluronidase (300 U/ml). Finally, the cells were separated by passing them through a 70 µm sieve, washed and transferred to cell culture.

FIG. 1 shows a plot of the donor cells (number) against the number of days of culturing, with the number behind/ after the curve giving the age of the human donor. This shows that diploid fibroblast cultures which were obtained, using this process, from donors who were younger than 60 years of age generally exhibited similar growth characteristics, with a mean doubling time of 4.3±0.6 days.

FIG. 2 shows a plot of the donor cells (number) against the number of days of culturing for human donors of different ages. In the figure, □ denotes preparation of the fibroblasts by enzymic treatment and Δ denotes isolation of individual cells simply by mechanical means. This shows that the fibroblast cultures which were prepared using the enzymic process clearly had a superior capacity for multiplication as compared with those fibroblast cultures which were obtained simply by mechanical treatment of the skin biopsy samples.

Using the novel process, diploid fibroblast cultures can be obtained not only from skin cells but also from peritoneal cells. It was found that cell cultures which were derived from the serosa initially grew in a similar manner to the cell cultures derived from the skin, with, however, the diploid fibroblasts originating from the serosa reaching the plateau at a markedly lower cell count than did the diploid skin fibroblast cultures of a comparable age. FIG. 3 shows a comparison of the cell counts plotted against the number of days of culturing fibroblast cultures which originate either from the skin (left-hand diagram) or the serosa (right-hand diagram) of donors aged from 45 to 59.

FIG. 4 shows the effect of so-called feeder cells on the plating efficiency of the diploid fibroblast cultures. Diploid skin-cell fibroblast cultures were prepared which were treated enzymically. Their plating efficiency was determined by sowing the cells at very low density on the cell culture bottles. Whereas the diploid fibroblasts without feeder cells exhibited hardly any colony formation under these conditions, it was possible to increase the plating efficiency to 9–24% by adding irradiated human fibroblasts of the WS-1 cell line.

EXAMPLE 3

Particular attention was devoted to the production of cytokines in the autologous diploid fibroblast cultures. For this purpose, culture supernatants were taken both from non-irradiated diploid fibroblasts and also from diploid fibroblasts which had been irradiated with 20 or 100 Gy. The culture supernatants were taken from the irradiated cells on the 3rd and the 8th day after irradiation.

Figure 5A:
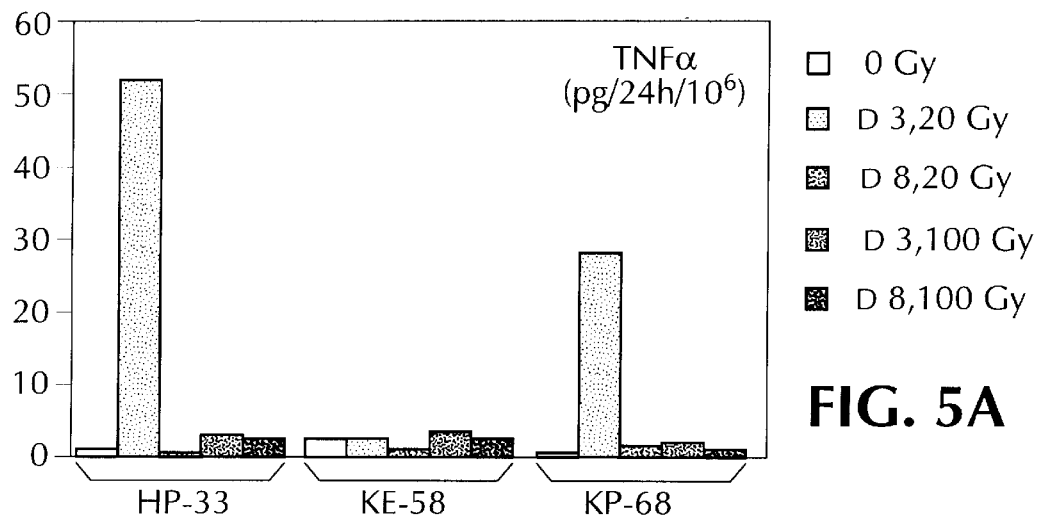
FIGS. 5A, 5E, and 5C depict the amount of TNFα, GM-CSF and IL-6 detected in the supernatants of irradiated and non-irradiated cell cultures. D=days; H=hours.
Figure 5B:
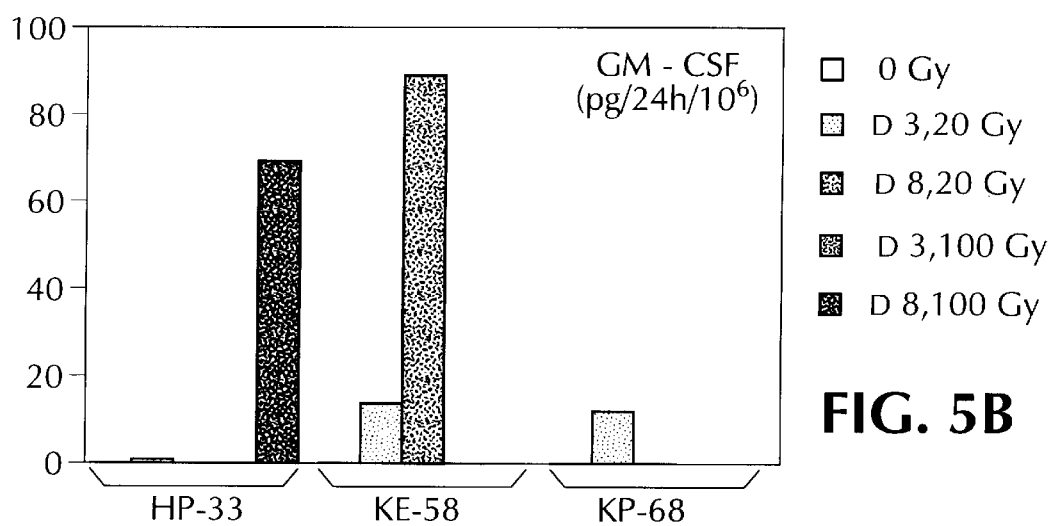
Figure 5C:
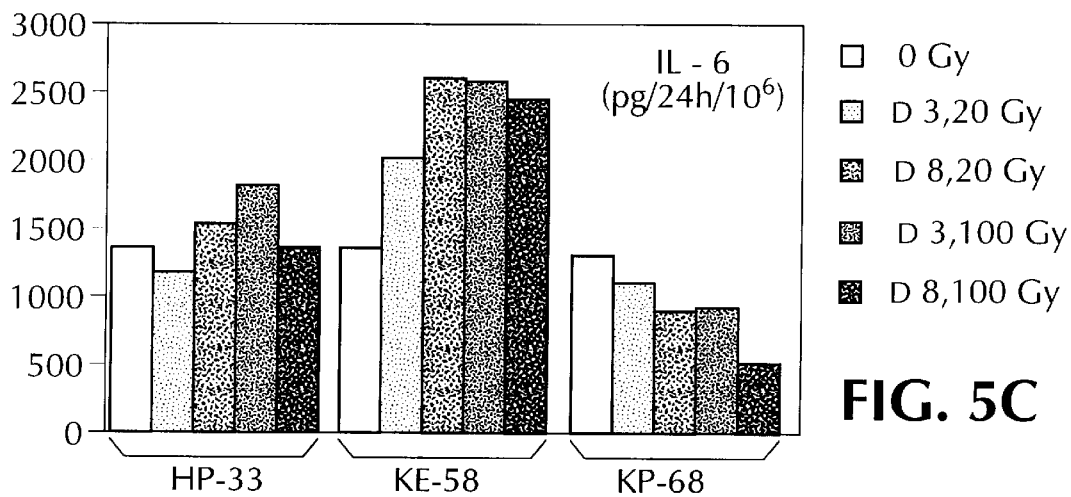

Between 1.2 ng and 20.5 ng of interleukin-6 were found, per 24 hours and $10^6$ cells, in the supernatants from non-irradiated diploid fibroblasts. The irradiation did not cause any significant changes in the secretion of IL6. More than one third of the cultures produced measurable amounts of GM-CSF (up to 3 ng/24 hours/$10^6$ cells) without significant change after irradiation. In contrast with this, the non-irradiated diploid fibroblasts did not produce any measurable quantities of TNFα, but up to 50 pg of TNFα were measured per 24 hours and $10^6$ cells in single cases following irradiation. These results are presented in FIG. 5, with the designations HP-33, KE-58 and KP-68 indicating different cell lines.

EXAMPLE 4

Preliminary experiments in a mouse model, which are explained in more detail below, were carried out in order to demonstrate the efficacy of the novel process for genetically transfecting human fibroblasts. The results from the mouse model can be applied in a corresponding manner to human fibroblasts.

a) Vector

The basic retroviral vector N2 is derived from the genome of the Moloney murine leukemia virus (MLV) and contains the bacterial gene for neomycin resistance as a selection marker. DNA fragments encoding the major immediate early human CMV promoter, the adenosine deaminase (ADA promoter), the poly-A signal and mouse GMCSF were cloned into different sites in the N2 vector. The construct N2 vector/CMV promoter/mouse GM-CSF was prepared by cloning the CMV-GM-CSF fusion product into a Xho I restriction site in the neomycin resistance gene in the N2 vector (FIG. 6, top).

In order to prepare the retroviral vector DC/AD/R/GM-CSF (FIG. 6, bottom), the ADA promoter was cloned in reverse orientation into a restriction cleavage site of the enzyme Mlu I which had been filled in using the Klenow fragment. The mouse GM-CSF cDNA was likewise cloned in reverse orientation into a cleavage site which had been produced by the restriction enzyme SnaB I, while the poly-A signal was cloned into an Apa I site in the 3'LTR polylinker which had been filled in using Klenow. The retroviral vectors were converted into the corresponding viruses by electroporating the vector DNA into a helper-free ecotropic packaging cell line (GP±E-86). Following selection on G418 (0.7 mg/ml genticin, Gibco Laboratory, Grand Island, N.Y.), colonies were isolated and expanded to form producer cell lines. Cell-free supernatant was tested on NIH 3T3 cells in order to determine the titer of the virus.

Figure 6:
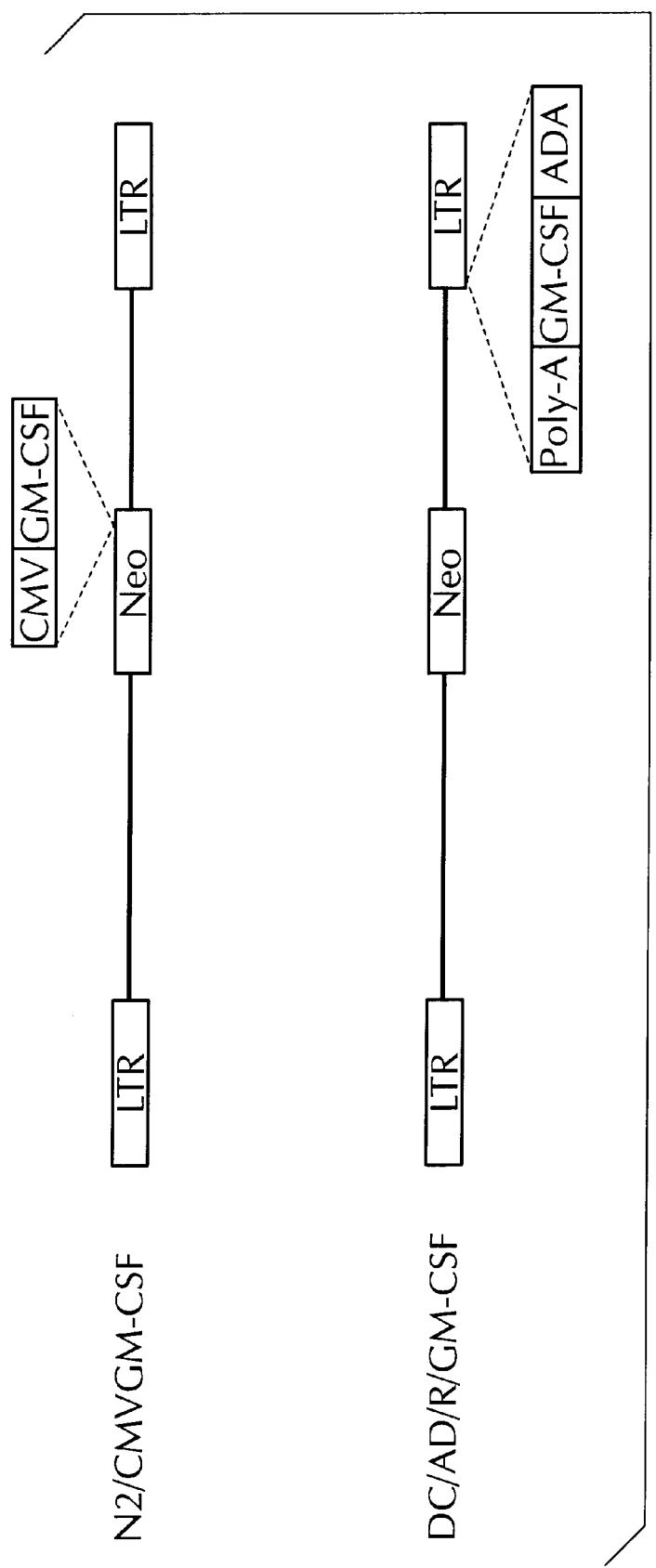
FIG. 6 depicts the structure of the retroviral vectors which were used.

FIG. 6 shows the structure of the retroviral vectors which were used.

b) Cell lines and infection of the tumor cells and fibroblasts

CMS5 is a methylcholanthrene-induced, non-metastatic fibrosarcoma from a BALB/c genetic back-ground. NIH 3T3 is a contact-inhibited fibroblast cell line which was established from NIH Swiss mouse embryos (CRL 1658). BALB 3T3 clone A31 are contact-inhibited, non-tumorogenic fibroblasts which were established from BALB/c mouse embryos (CCL 163). Both the fibroblast cell lines were obtained from ATCC. The cells were cultured in Dulbeccols modified Eagle's medium which was supplemented with 10% fetal calf serum, 100 U/ml penicillin, 100 µg/ml streptomycin and 2 mmol/l L-glutamine. Virus-producer cell lines, which secreted high titers of the virus, were employed for infecting the CMS5 cells and the fibroblast cells. Following selection with G418, clones or bulk-infected cells were expanded into lines and subjected to further analysis.

c) Cytokine determination

Secretion of GM-CSF into the supernatants of retrovirally infected CMS5 cells and fibroblasts, and the concentration of GM-CSF in the serum of treated mice, were determined by a bioassay and confirmed using an ELISA test. The supernatants from semi-confluent parenteral or GM-CSF-secreting cells were collected after 24 hours, with the cell count being determined and the supernatant being examined for the production of mouse GM-CSF.

$10^6$ CMS5 cells which were irradiated with 50 Gy or $10^6$ cells which were transfected with the vector N2/CMV/GM-CSF/CMS5 were examined. On the day of irradiation, the cells were plated in small tissue culture bottles and the quantity of GM-CSF in the 24-hour culture supernatant was determined on the 3rd, 6th, 9th and 12th day following the irradiation.

The biological activity of the GM-CSF to be investigated was determined by ascertaining the ability of the GM-CSF-containing supernatants to induce the incorporation of $^3$H-thymidine into the DNA of GM-CSF-de-pendent mouse 32DC13 cells. After the cells had been incubated overnight without GM-CSF, $10^4$ cells were incubated in each well of a 96-well microtiter plate together with dilutions of the test liquids and the cells were cultured at 37° C. for 6 hours and in 6% $CO_2$. After that, 1 µCi of $^3$H-thymidine was added and the incubation was continued at 37° C. for a further 15 hours. After having been washed, the cells were evaluated using a liquid scintillation counter. The GM-CSF activity was expressed as counts per minute (cpm) and the production, in ng per 24 hours, by $10^6$ cells was calculated by comparison with a standard curve of recombinant mouse GM-CSF. In addition to this, the production of the GM-CSF was confirmed by means of an ELISA test.

Figure 7:
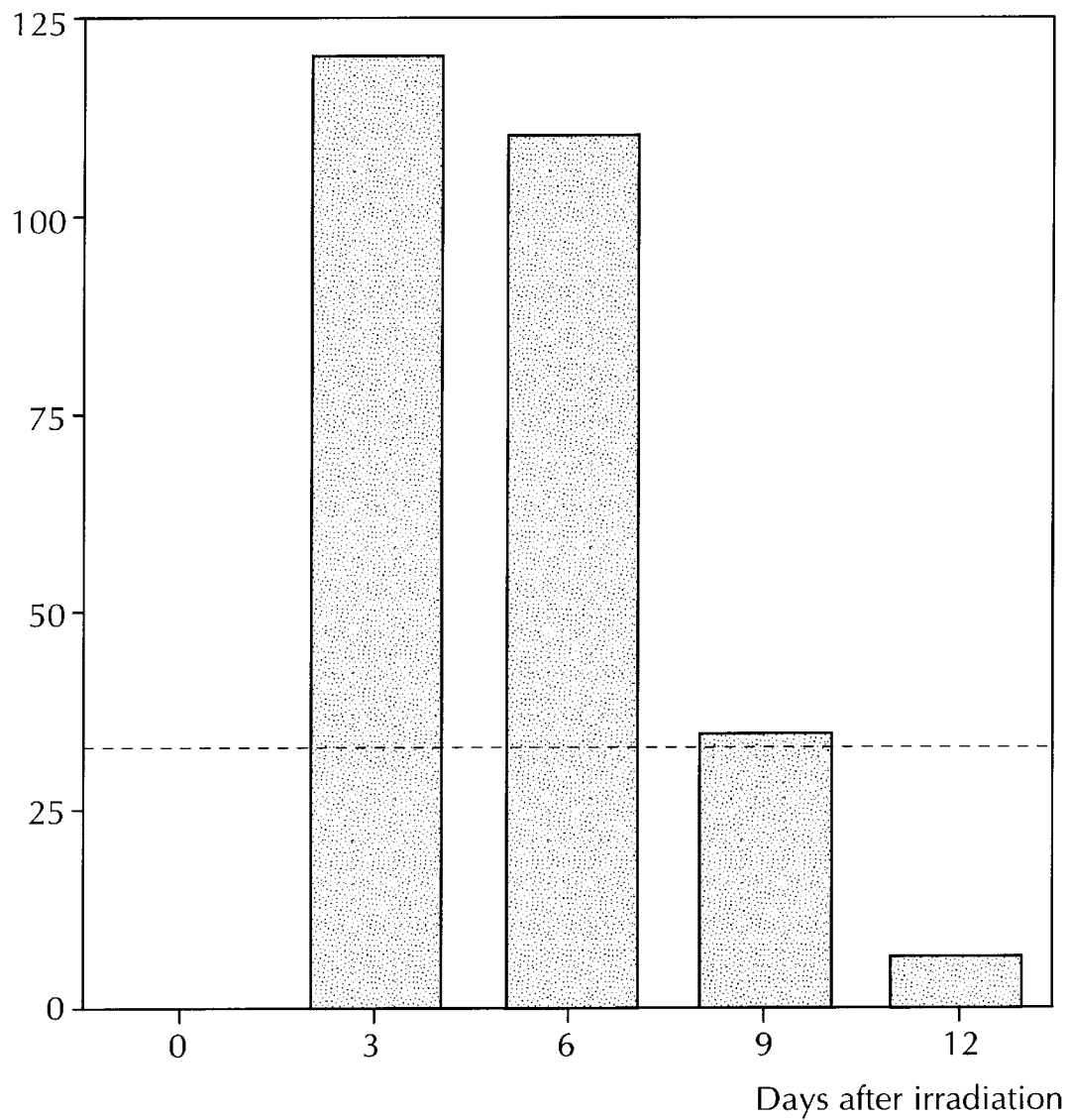
FIG. 7 depicts GM-CSF production (ηg/24 hr) by N2/CMV-GM-CSF/CMS 5#6 cells after irradiation with. 50 Gy. $10^6$ irradiated cells were plated on day 0 and the GM-CSF concentration in the 24 h culture supernatant was determined in a bioassay.

The irradiation of growth factor-producing autologous or allogenic cells may be used for preventing further proliferation of the cells following injection in vivo. For this reason, GM-CSF-secreting cells were first irradiated with 50 Gy and the secretion of GM-CSF was then determined up to 12 days after irradiation. It can be seen from FIG. 7 that the production of GM-CSF was initially increased following irradiation. Whereas approximately 40 ng/$10^6$ cells/24 hours were measured prior to irradiation, the values are approximately 130 ng/$10^6$ cells/24 hours on the 3rd and 6th days after irradiation. On the 9th day, the values fall back to those obtained prior to irradiation, and the production of GM-CSF/24 hours is approximately one-third of the starting value on the 12th day after irradiation. Since the number of surviving cells has already fallen to one-tenth of the starting value on the 6th day, it is clear that GM-CSF is still being liberated from cells which are no longer vital. d) Transfer of the genetically transfected cells into mice Female BALB/c mice which were 7–10 weeks old were employed for the experiments. On day 0 and day 2, all the mice were given 150 mg/kg cyclophosphamide, which was administered intraperitoneally. While one group of mice were not given any further injections, a second group was injected subcutaneously twice on day 3 with 100 ng of recombinantly prepared mouse GM-CSF. On day 3, the latter group was given a total of $10^7$ N2/CMV/GM-CSF-CMS5 cells, which had been irradiated with 50 Gy, which cells were injected subcutaneously at two sites. From the fourth day onwards, blood was transferred daily from the tail veins of the mice into heparinized Eppendorf tubes. The number of leucocytes was determined in a Neubauer cell chamber after lyzing the erythrocytes. Differential blood pictures were prepared every two days, with the differential blood picture being determined after staining with MayGrünwald-Giemsa. Serum values of mouse GM-CSF were determined on days 1, 4 and 10 after injecting the irradiated GM-CSF-secreting fibrosarcoma cells.

EXAMPLE 5

Female BALB/c mice were treated as described in Example 4d. From the 3rd day onwards, the peripheral leucocyte counts were ascertained daily and a differential blood picture was prepared every 2 days. In these. mouse strains, the basic leucocyte counts are from about 9000 to 10,000 leucocytes/$\mu$l. As a result of administering cyclophosphamide, the leucocytes declined on the 3rd day down to about 1000 to 1500 leucocytes/$\mu$l. No major changes in the leucocyte values were evident. up to the 6th day after injecting cyclophosphamide. All the treatment groups exhibit approximately the same values. From the 7th day onwards, a difference in the absolute leucocyte count can be seen between the GM-CSF-treated mice and the control mice which were only injected with cyclophosphamide. After subcutaneous injection or single injection of GM-CSF-secreting autologous cells, the values in the growth factor-treated animals are, on the 7th and 8th days after beginning the treatment, approximately twice as high as in the control mice. The groups treated with recombinant growth factor, like the animals treated with GM-CSF-secreting fibroblasts, achieve the normal leucocyte values on the 8th day after the cyclophosphamide injection. By contrast, the control mice are still exhibiting values which are half the normal. FIG. 8 gives the differential blood pictures of the different treatment groups as absolute leucocyte subpopulations (monocytes, granulocytes and lymphocytes). In the differential blood picture, approximately 1% monocytes, 15–30% granulocytes and 70–85% lymphocytes are present in untreated BALB/c mice. On the 5th day after beginning the cyclophosphamide treatment, that is in the phase of absolute neutropenia, virtually only lymphocytes can be found in the differential blood pictures in all treatment groups. A clear difference in the differential blood pictures can also be observed on the 7th day, when the absolute leucocyte values of the mice treated with recombinant GM-CSF and with GM-CSF-secreting cells are approximately twice as high as they are in the animals which have only been treated with cyclophosphamide. The animals which have not been treated with growth factor have only about 15% of the monocytes and 25% of the granulocytes possessed by the mice which were treated subcutaneously with GM-CSF or with GM-CSF-secreting fibroblasts and which have already reached normal absolute granulocyte counts. No differences in the absolute lymphocyte values can be observed between the different treatment groups.

FIG. 8 consequently demonstrates that even a single injection of irradiated, genetically transfected autologous cells has biological effects on the blood picture of chemotherapeutically treated mice.

EXAMPLE 6

Figure 9:
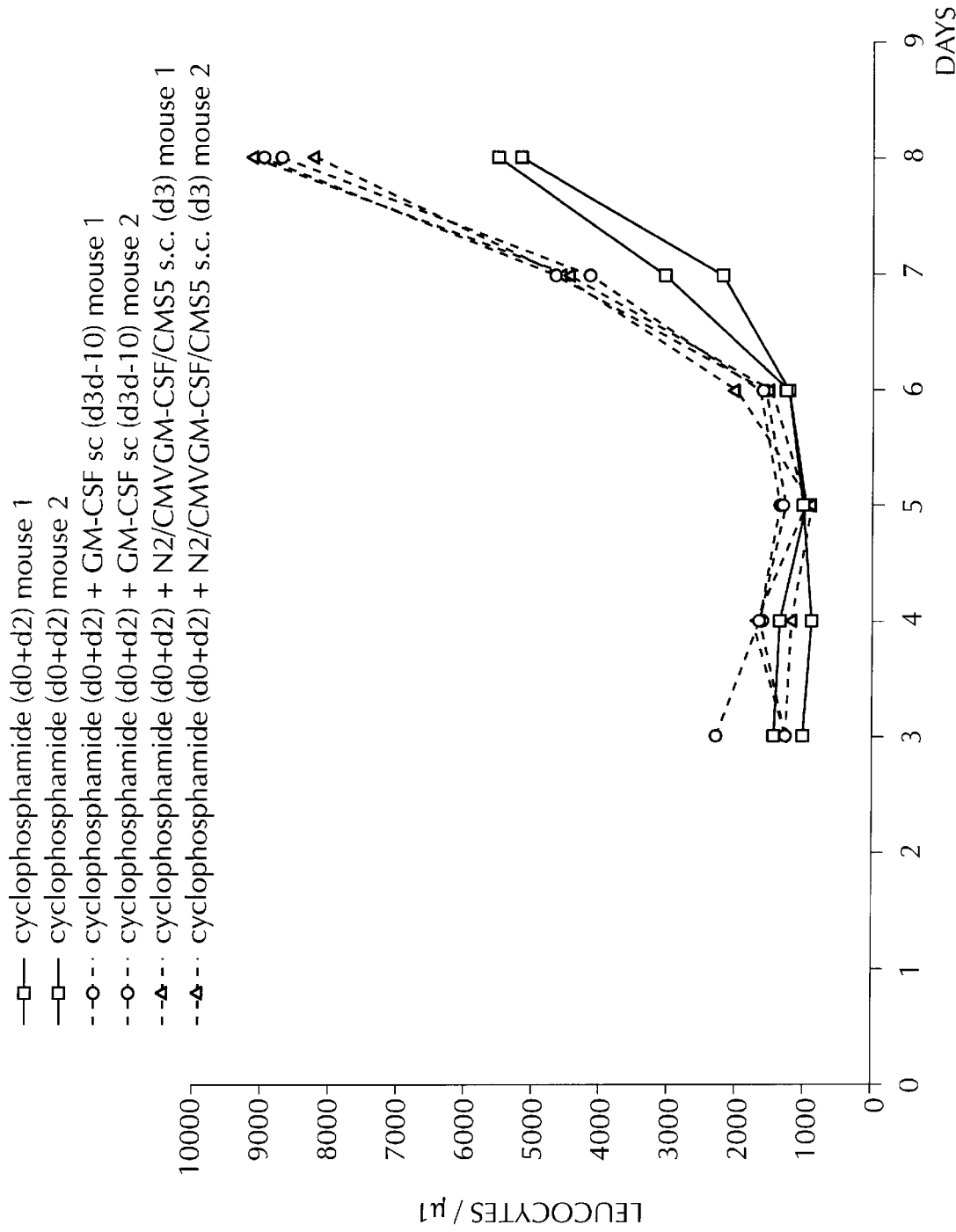
FIG. 9 depicts the peripheral leucocyte counts in cyclosphosphamide-treated BALB/c mice with and without treatment with mGM-CSF or GM-CSF secreting fibrosarcoma cells.
Figure 10B:
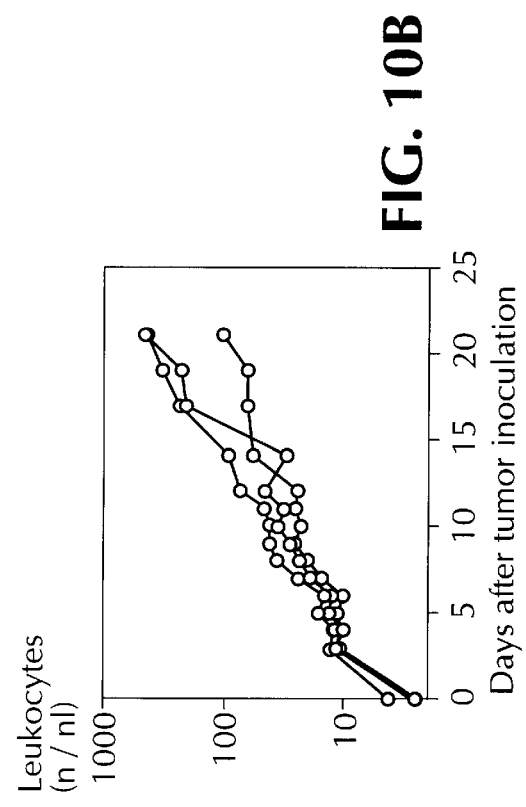
FIGS. 10A, 10B, 10C, 10C, and 10D depict the leucocyte count as numbers of cells per ηl as a function of time after inoculation with non-irradiated CMS-5 cells transfected with pCMV.GCSF iresNEO (FIGS. 10A and 10C) or pCMV.GCSF iresTK/NEO (FIG. 10B and 10D).
Figure 10D:
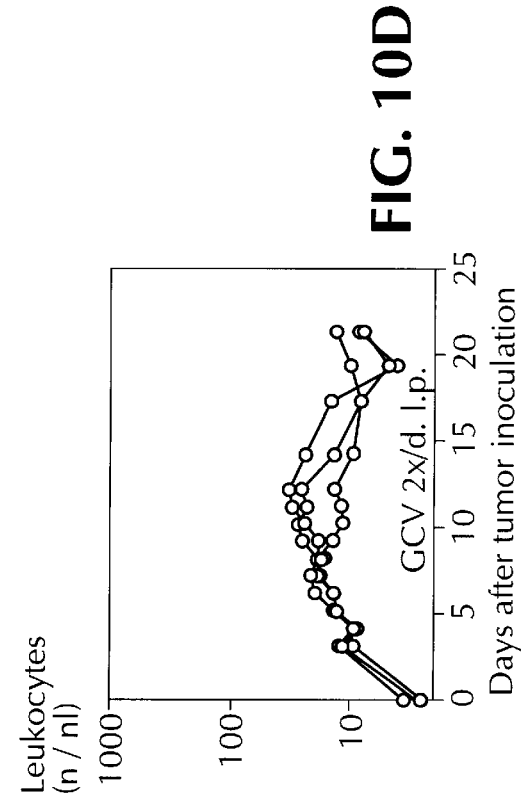
Figure 10A:
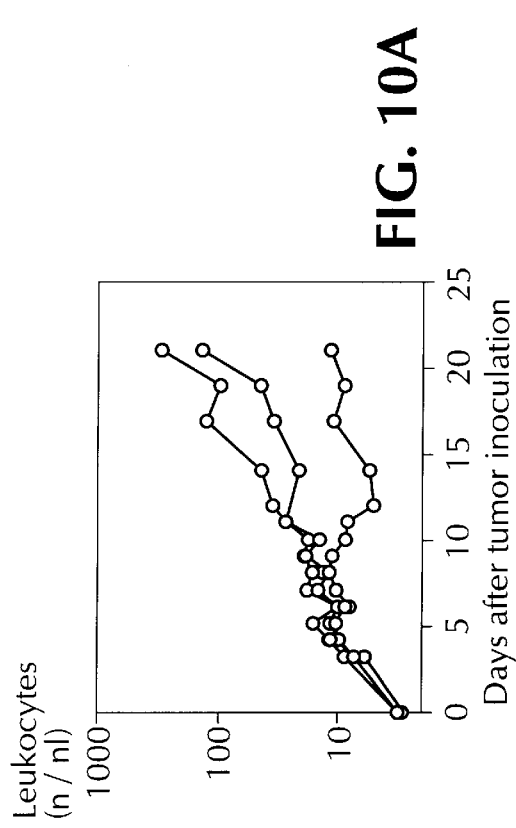
Figure 10C:
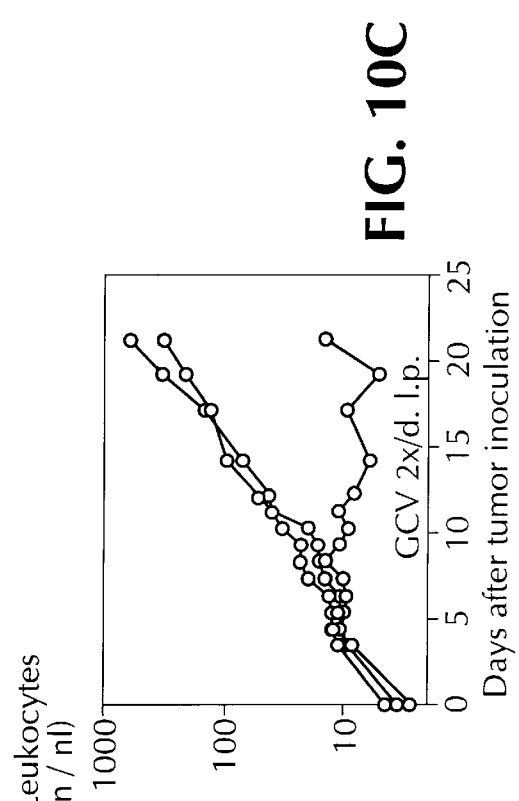
Figure 10F:
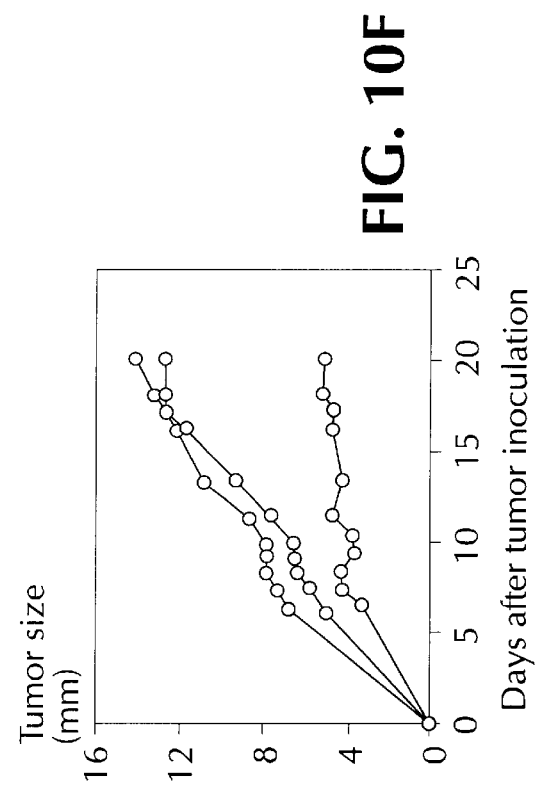
FIGS. 10E, 10G, 10F, and 10H depict the chronological development of tumor size in BALB/c mice after inoculation with non-irradiated CMS-5 cells transfected with pCMV. GCSF. iresNeo (FIGS. 10E and 10G) or pCMV. GCSF iresTK/Neo (FIGS. 10F and 10H).
Figure 10H:
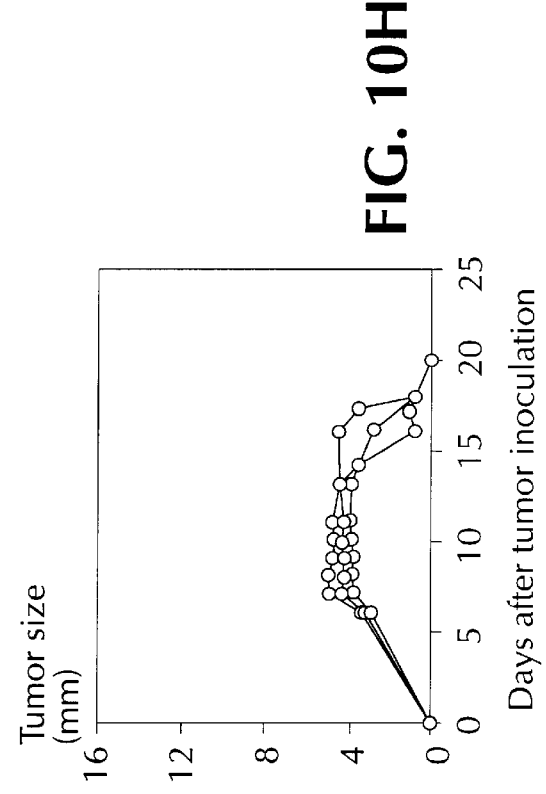
Figure 10E:
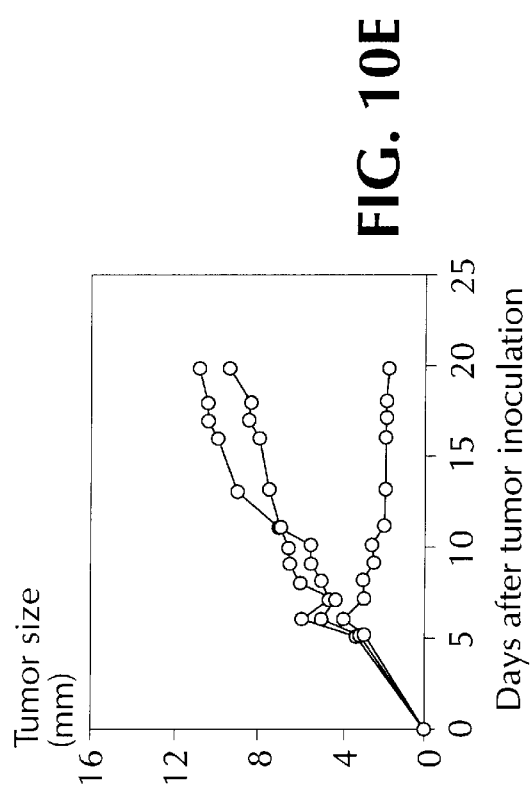
Figure 10G:
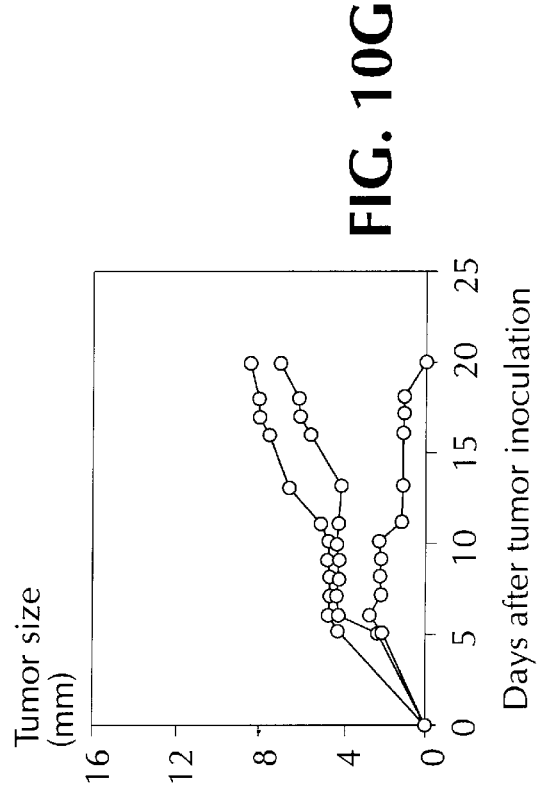

FIG. 9 depicts the leucocyte count, which changes over the course of time. The mice were in each case treated with cyclophosphamide. One control group did not receive any GM-CSF. In a further control group, recombinantly prepared GM-CSF was injected subcutaneously. In the third group, genetically transfected cells which produced GM-CSF were administered subcutaneously.

EXAMPLE 7

Selective destruction of genetically transfected cells in vivo. In this example, murine CMS-fibrosarcoma cells containing 2 different constructs were transfected:
1. pCMV.GCSF.iresNEO contains, under the control of the CMV promoter, the human G-CSF gene and, by way of an IRES (internal ribosomal entry site) the gene for resistance to neomycin. In this case, therefore, the intention is to express G-CSF and neomycin phosphotransferase.
2. pCMV.GCSF.iresTK/NEO contains, under the control of the CMV promoter, the G-CSF gene and also, by way of an IRES, a herpes simplex virus thymidine kinase/neomycin resistance gene fusion. In this case, the intention is to express TK in addition to G-CSF and neomycin phosphotransferase and, as a consequence, to phosphorylate and activate gancyclovir after this prodrug has been administered.

FIGS. 10A 10C 10B and 10D shows a plot of the leucocyte count as numbers of cells per nl (n/nl) against time (in days) after subcutaneously inocculating 2.5×$10^5$ non-irradiated CMS-5 cells of the previously mentioned construct 1 10A, 10C, 10E, and 10G and of construct 2 10B, 10D, 10F, and 10H into the tumors of 3 BALB/c mice. The chronological course of the leucocyte counts following the tumor inoculations is shown at the bottom left and bottom right of the diagrams, with in this case the prodrug gancyclovir also having been administered i.p. twice daily. The chronological development (in days) of tumor size (mm) is given for the same constructs, once again in three BALB-c test mice, in FIGS. 10E, 10G, 10F, and 10H.

The two groups of BALB-c mice were in each case injected subcutaneously with 2.5×$10^5$ non-irradiated CMS-5 cells which had been transfected with the above-mentioned vectors. From the seventh day (d7) onwards, one group of the mice in each case was given gancyclovir (GCV) i.p.

twice daily (see FIG. 10C, 10D, 10G, and 10H). The leucocyte values and the development of tumors were monitored. The experimental group, which was treated with GCV and received CMS-5 cells which were transfected with p.CMV.GCSF.iresTK/NEO, exhibits a decline in leucocytes and regression of the tumor (see FIG. 10D and 10H right). This demonstrates that even tumor cells which have been transfected with the TK gene can be selectively switched off in vivo by means of the "suicide gene" expression mechanism. Side effects were not observed in the mice, which are also tumor-free at 5 weeks after terminating the GCV administration.

EXAMPLE 8

Reconstitution of hematopoiesis after a single subcutaneous injection of fibroblasts which have been transfected with the G-CSF gene. (Transfection of fibroblasts using physical methods of gene transfer, in this case lipofection, in this case illustrated using the example of human G-CSF).

Figure 11B:
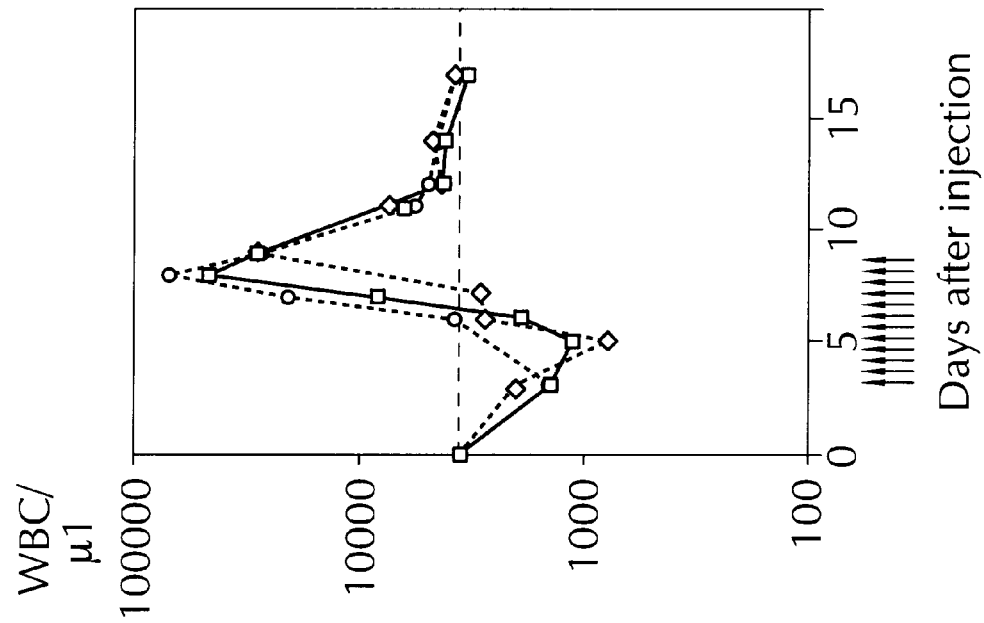
FIG. 11B, Cyclophosphamide+rhG-CSFbbid.
Figure 11A:
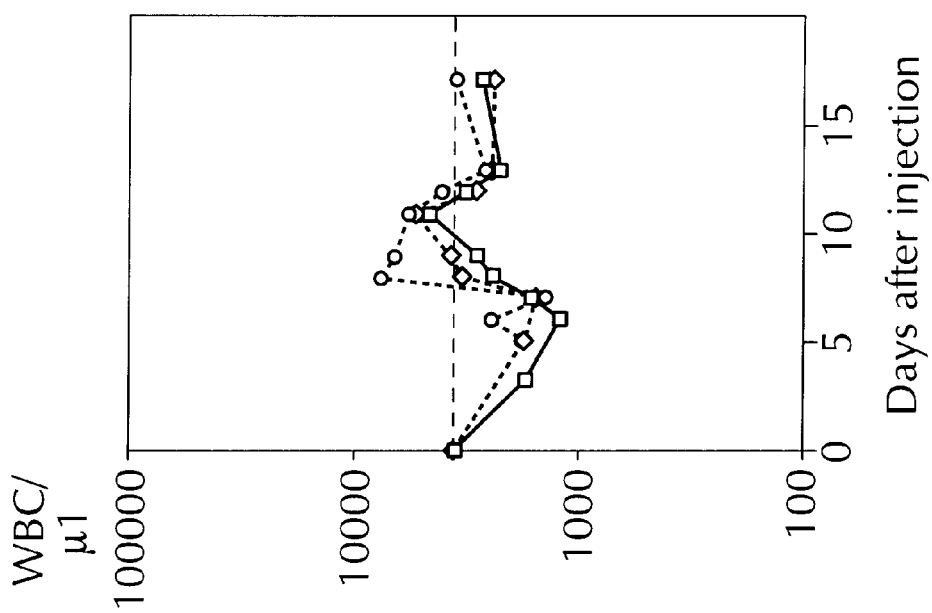
FIG. 11A, Cyclophosphamide.

FIG. 11 shows a plot of leucocyte numbers (WBC/$\mu$l) against time after injection (in days) following chemotherapy and cytokine therapy in the presence/absence of transfected fibroblasts. The chronological course when cyclophosphamide alone is administered is shown on the left-hand side, while the corresponding chronological course when cyclophosphamide is administered together with the twice-daily subcutaneous administration of recombinant human G-CSF, termed rhG-CSF for short below, is shown center left. The chronological course of leucocyte counts following administration of cyclophosphamide and a single injection of $5 \times 10^6$ G-CSF-gene-transfected BALB-3T3 fibro-blasts can be seen in the center right on the diagram, while the chronological course of leucocyte counts following the administration of cyclophosphamide and a single injection of $5 \times 10^6$ irradiated G-CSF-gene-transfected BALB/3T3 fibroblasts can be seen on the right-hand side. In these plots, the curves marked with a square, a rhombus and circle represent the changes in the leucocyte contents of the three test mice employed. It is evident from the three diagrams that the regeneration of the leucocytes takes place at least as rapidly in the groups in which there was a single injection of the transfected fibroblasts (center right and right) as when there was a twice-daily subcutaneous injection of the recombinant protein (center left).

The following table shows the effect of G-CSF administration on the mobilization of hematopoietic stem cells into the peripheral blood. This table compares the day on which all of the mice of the group (in each case three mice per group) exhibited at least 3500 leucocyte/$\mu$l and the corresponding values on the following day. In addition, the table gives the number of colony forming cells, i.e. of cells which provide information on the number of hematopoietic stem cells, termed CFU for short below, and also the values of the CFU to leucocyte ratios in the four different treatment groups. It can be seen that a single injection of nonirradiated and also irradiated G-CSF-gene-transfected fibroblasts makes possible a mobilization of hematopoietic stem cells into the peripheral blood which is comparable to that obtained with the twicedaily subcutaneous injection of rhG-CSF. This is of clinical interest since, in the case of the stem cell transplantation which is employed following high-dose chemotherapy in patients possessing a variety of tumors, these stem cells have to be collected, for example, by means of leukophoresis. Following low-dose chemotherapy, the patients are currently given G-CSF subcutaneously over several days (as discussed in connection with the above animal model) for this purpose.

However, this form of parenteral administration is not only technically elaborate but also much more expensive. It would be desirable, therefore, to replace the frequent subcutaneous injections with a single injection.

| Effect of G-CSF administration on mobilization of hematopoietic stem cells into the peripheral blood. | | | | | | |
|---|---|---|---|---|---|---|
| | Day x | | | Day x + 1 | | |
| | Leucocytes | CFU/$\mu$l | CFU/Leucocytes | Leucocytes | CFU/$\mu$l | CFU/Leucocytes |
| Cyclophosphamide | 5533 ± 348 | 18 ± 3.8 | 0.333 ± 0.109 | 6067 ± 354 | 4 ± 1.3 | 0.060 ± 0.016 |
| + G-CSF s.c. | 6500 ± 1021 | 35 ± 4.5 | 0.600 ± 0.081 | 16767 ± 1573 | 66 ± 13.9 | 0.400 ± 0.047 |
| + G-CSF/BALB s.c. | 4183 ± 261 | 10 ± 4.7 | 0.200 ± 0.081 | 9700 ± 1510 | 46 ± 9.6 | 0.467 ± 0.072 |
| + irradiated G-CSF/BALB s.c. | 7483 ± 1204 | 29 ± 1.9 | 0.400 ± 0.047 | 12800 ± 1746 | 90 ± 8.0 | 0.733 ± 0.072 |

The ± values mentioned above for leucocytes, CFU and CFU following the value are the corresponding standard errors.
The following were administered to the mice:
cyclophosphamide: d0 + d2 (i.p. 150 mg/kg)
+ G-CSF: cyclophosphamide + rhG-CSF d3–d7 (s.c. 125 $\mu$g/kg, 2 × daily)
+ G-CSF/BALB: cyclophosphamide + hG-CSF-gene-lipofected BALB 3T3, d3 (s.c. $5 \times 10^6$ cells)
+ irradiated G-CSF/BALB: cyclophosphamide + irradiated (50 Gy) hG-CSF-gene-lipofected BALB 3T3, d3 (s.c., $5 \times 10^6$ cells).

We claim:

1. A process for producing transfected fibroblasts, comprising:
    (a) removing a fibroblast containing tissue sample from a subject,
    (b) preparing a suspension of single cells of said tissue sample,
    (c) washing said suspension,
    (d) culturing the washed cells in the presence of feeder cells selected from the group consisting of irradiated human fibroblasts and irradiated murine fibroblasts, under conditions favoring proliferation of fibroblasts from said sample to produce clonogenic fibroblasts, and
    (e) inserting at least one gene into said clonogenic fibroblasts wherein said gene encodes a biologically active protein.

2. The process of claim 1, wherein said biologically active protein is a therapeutically active protein.

3. The process of claim 2, wherein said therapeutically active protein is selected from the goup consisting of a growth factor, a hormone, an enzyme, a coagulation factor or a coagulation inhibitor.

4. The process of claim 3, wherein said growth factor is a hematopoietic growth factor.

5. The process of claim 1, further comprising transfecting said fibroblasts with a suicide gene.

6. The process of claim 5, wherein said suicide gene is a herpes simplex virus thymidine kinase gene.

7. The process of claim 1, wherein said gene is operably linked to a promoter.

8. The process of claim 1, wherein said gene is inserted by a method selected from the group consisting of electroporation, microinjection, particle bombardment and lipofection.

9. The process of claim 1, wherein said fibroblasts are human fibroblasts.

10. The process of claim 1, wherein said feeder cells are allogeneic to a subject from which they are taken.

11. The process of claim 1, further comprising contacting said tissue sample with at least one enzyme selected from the group consisting of collagenase, dispase, and hyaluronidase.

12. The process of claim 7 wherein said promoter is an inducible promoter.

13. The process of claim 1 wherein said fibroblast containing tissue is a biopsy from a patient having cancer.

14. The method of claim 1 further comprising (f) isolating and expanding a transfected cell of step (e).

15. A process for producing clonogenic fibroblasts, comprising:
   (a) removing a fibroblast containing tissue sample from a subject,
   (b) preparing a suspension of single cells of said tissue sample,
   (c) washing said suspension,
   (d) culturing the washed cells in the presence of feeder cells selected from the group consisting of irradiated human fibroblasts and irradiated murie fibroblasts, under conditions favoring proliferation Qf fibroblasts from said sample to produce clonogenic fibroblasts, and
   (e) isolating and then expanding the isolated clonogenic fibroblasts.

16. A method for mobilizing hematopoietic cells in a subject comprising administering to a subject in need thereof an amount of a therapeutic composition comprising transfected fibroblasts produced by the method of claim 7 and a pharmaceutically acceptable carrier wherein said biologically active protein is granulocyte macrophage colony stimulating factor (GM-CSF) and wherein said amount is sufficient to mobilize hematopoietic cells.

17. The method of claim 16 wherein administering the transfected fibroblasts comprises the step of implanting a vessel prosthesis comprising a biocompatible material containing the transfected fibroblasts into said subject.

18. The method of claims 16 wherein said transfected fibroblasts are irradiated.

19. The method of claim 18 wherein administering the transfected fibroblasts comprises the step of implanting a vessel prosthesis comprising a biocompatible material containing the transfected fibroblasts into said subject.

20. A method for mobilizing hematopoietic cells in a subject comprising administering to a subject in need thereof an amount of a therapeutic composition comprising transfected fibroblasts produced by the method of claim 7 and a pharmaceutically acceptable carrier wherein said biologically active protein is granulocyte colony stimulating factor (G-CSF) and wherein said amount is sufficient to mobilize hematopoietic cells.

21. The method of claim 20 wherein said transfected fibroblasts are irradiated.

22. The method of claim 20 wherein administering the transfected fibroblasts comprises the step of implanting a vessel prosthesis comprising a biocompatible material containing the transfected fibroblasts into said subject.

23. The method of claim 21 wherein administering the transfected fibroblasts comprises the step of implanting a vessel prosthesis comprising a biocompatible material containing the transfected fibroblasts into said subject.

* * * * *